United States Patent [19]

Olrik et al.

[11] 4,306,454

[45] Dec. 22, 1981

[54] METHOD AND AN APPARATUS FOR METERING A LIQUID FLOW

[75] Inventors: Henrik-Gerner Olrik, Humlebaek; Per Salling, Birkerod, both of Denmark

[73] Assignee: A/S N. Foss Electric, Hillerod, Denmark

[21] Appl. No.: 91,034

[22] Filed: Nov. 5, 1979

[30] Foreign Application Priority Data

Nov. 3, 1978 [DK] Denmark .................... 4923/78

[51] Int. Cl.³ ........................................ G01F 11/00
[52] U.S. Cl. ........................................ 73/224
[58] Field of Search .......................... 73/224, 225

[56] References Cited

U.S. PATENT DOCUMENTS

| | | | |
|---|---|---|---|
| 1,433,870 | 10/1922 | Bowden | 73/224 |
| 1,548,166 | 8/1925 | Peters | 73/224 X |
| 1,592,968 | 7/1926 | Daly | 73/225 |
| 3,040,576 | 6/1962 | Vogel | 73/224 |

FOREIGN PATENT DOCUMENTS 261813  5/1970  U.S.S.R. ...................... 73/224

*Primary Examiner*—Herbert Goldstein

*Attorney, Agent, or Firm*—Dennison, Meserole, Pollack & Scheiner

[57] ABSTRACT

A method and an apparatus for metering a flow of a liquid, such as a milk flow in a milking system. The liquid is passed into a metering or measuring chamber from which it is discharged in portions having substantially the same mass or weight, and the total number of liquid portions discharged is counted whereafter the total mass or weight of the liquid flow may be calculated on the basis of that count.

The discharge operation is controlled by a float member arranged within the metering chamber and containing a magnet which may actuate reed switches positioned at different levels along the metering chamber. Each liquid portion is discharged from the metering chamber by exposing the chamber to a gas pressure substantially exceeding the pressure at the discharge end of a metering chamber outlet. The metering chamber is preferably partly defined by a bell-shaped valve body controlling the metering chamber inlet and being movable to its closed position under the influence of said gas pressure. The apparatus may contain special means for metering a last fraction of a liquid portion as well as means for reducing formation of foam within the metering chamber.

48 Claims, 14 Drawing Figures

METHOD AND AN APPARATUS FOR METERING A LIQUID FLOW

BACKGROUND OF THE INVENTION

1. Field of the Invention

The present invention relates to a method and an apparatus for metering a flow of a liquid or for determining the mass or weight thereof

2. Description of the Prior Art

U.S. Pat. No. 4,030,356 discloses a continuous weighing mechanism, wherein the liquid flow to be weighed is supplied to a liquid receiver comprising two liquid receiving trays mounted on a common rocker shaft. When one tray has been filled with liquid the shaft rotates, whereby the other tray is moved to a liquid filling position while said one tray is being emptied. The mass of the liquid having passed the liquid receiver is calculated on the basis of the number of the rocking movements registered by an electric circuit. The accuracy of measurement of this known apparatus is, however, less satisfactory when the liquid flow to be measured varies, because varying liquid flow causes that the rocking liquid receiving trays will be influenced by varying forces of inertia.

U.S. Pat. Nos. 2,853,877 and 3,937,083 and British patent specification No. 1,089,159 disclose liquid metering devices comprising a metering or measuring chamber having a float member arranged therein. The measuring chamber has an inlet and an outlet with inlet and outlet valves, respectively. The liquid to be measured is passed into the measuring chamber through the inlet while the outlet is closed by the outlet valve. When the liquid supplied to the measuring chamber has moved the float member to a predetermined upper level it causes the inlet valve to be closed and the outlet valve to be opened so that the liquid may flow out of the measuring chamber through its outlet under the influence of its own gravity. When the float member has been moved downwardly to a predetermined lower position the outlet valve is closed while the inlet valve is open, and the operation just described is thereafter repeated. Due to the fact that the liquid is discharged from the measuring chamber through the outlet valve exclusively under the influence of its own gravity the capacity of the known metering apparatuses described above is rather limited.

SUMMARY OF THE INVENTION

The present invention provides a method of metering a liquid flow, said method comprising: (a) passing said liquid flow into a measuring chamber containing floating means movably arranged therein and including liquid inlet and outlet passages, said outlet passage opening into said measuring chamber at the lower part thereof, (b) discharging said liquid from said measuring chamber through said outlet passage in portions, the discharge of each portion being initiated in response to a predetermined upward movement of said floating means and caused by closing said inlet passage and exposing said measuring chamber to a gas pressure exceeding the pressure at the discharge end of said outlet passage, and (c) counting the number of portions discharged.

Due to the pressure difference created between the measuring chamber and the discharge end of the outer passage the discharge operation may be accelerated and supply of said gas pressure to the measuring chamber may be used for further purposes as explained in the following.

In case the discharge end of the outlet passage is exposed to atmospheric pressure the said pressure difference during the discharge operation may be optained by supplying pressurized air or gas to the measuring chamber. However, in a preferred embodiment of the method according to the invention the measuring chamber as well as the discharge end of the outlet passage is exposed to vacuum when liquid is passed into the measuring chamber through the inlet thereof, while the discharge operation is initiated by supplying atmospheric pressure to the measuring chamber. An inlet valve arranged in said inlet passage and/or the supply of gas pressure to the measuring chamber may be controlled by the position of said floating means in the measuring chamber. Thus, the supply of gas pressure may be initiated and the inlet valve may be closed when the floating means reach a predetermined upper position in the measuring chamber.

The inlet valve means preferably comprise an inlet valve member movable between opening and closing positions, and the said inlet valve member is then preferably adapted to be moved to its closing position by means of the gas pressure supplied to the measuring chamber.

When the method according to the invention is used for metering a flow of milk or another liquid which is liable to foam the formation of foam within the measuring chamber may cause a certain inaccuracy in measurement. Therefore, it is desired to suppress and reduce the foam formation in the measuring chamber to the highest possible extent. Thus, the inlet passage may contain foam separating or reducing means. Furthermore, each discharge of liquid from the measuring chamber may comprise an initial foam reducing step. Thus, the discharge of liquid from the measuring chamber under the influence of pressurized gas or atmospheric pressure supplied thereto may initially take place through a small bypass opening communicating with the liquid inlet passage while the outlet passage is closed, for example by means of suitable valve means arranged therein. When a certain smaller amount of liquid has been discharged through the bypass opening so that the floating means has reached a predetermined second level somewhat below the first level at which the supply of gas pressure to the measuring chamber is initiated, the outlet valve is opened and the liquid portion remaining in the measuring chamber and including substantially no foam is discharged through the outlet passage. Because of the suppression of foam in the measuring chamber and because the floating means will move very slowly downwardly from the said first to the said second slightly lower level this second level may be determined with great accuracy so that the weight or mass of the liquid portions discharged through the outlet passage will be almost identical, whereby a high accuracy of measurement may be obtained.

When a liquid flow being measured stops the amount of liquid present in the measuring chamber may constitute only a fraction of the liquid portion normally discharged from the measuring chamber. Thus, the floating means does not reach the level at which liquid discharge is initiated. Therefore, discharge of such last fraction may be initiated manually, and the amount or weight of that last fraction of a liquid portion may be determined on the basis of the time used for discharging said fraction. In order to obtain a relatively long discharge period and, consequently, an increased accuracy of measurement the fraction is preferably discharged through an opening or passage having a relatively small cross sectional area. In the preferred embodiment of the invention the said last fraction is discharged through the bypass opening mentioned above.

The method according to the invention may, for example, be used for measuring milk flowing from the teat cups of a milking machine. Substantial variations in the vacuum at the teat cups of a milking machine may adversely influence the yield of the cows being milked. The occurrence of solid milk columns in the conduits between the vacuum line and the teat cups may create such variations in the vacuum, and in order to avoid the formation of such milk columns a venting opening for sucking in "false air" is normally present at the teat cups. As explained above, the foam formation is preferably suppressed or reduced before the liquid or milk is passed into the measuring chamber, which means that air entrained by the liquid is separated therefrom. In order to avoid formation of solid columns downstream of the measuring chamber air may be mixed with milk discharged therefrom.

The method according to the invention makes it possible to obtain a representative sample of the total liquid flow. Thus, a small sample fraction of each milk portion discharged from the measuring chamber may be taken out through a sample conduit branched off from the outlet passage. Such sample consisting of several sample fractions will be representative for the total amount of liquid having passed the outlet passage from the measuring chamber, and the sampling method described will be almost insensitive to the orientation of the outlet passage.

The present invention also provides an apparatus for metering a liquid flow, said apparatus comprising: (a) a measuring chamber having liquid inlet and outlet passages, said outlet passage opening into the lower part of said measuring chamber, (b) floating means movably arranged within said chamber, (c) discharge means for discharging said liquid from said measuring chamber through said outlet passage in portions, said discharge means being adapted to initiate discharge of each portion in response to a predetermined upward movement of said floating means by closing said liquid inlet passage and exposing said measuring chamber to a gas pressure exceeding the pressure at the discharge end of said outlet passage, and (d) means for counting the number of portions discharged. The apparatus preferably also comprises calculating and registering means for calculating and registering the amount or weight of the total liquid flow having passed through the apparatus.

BRIEF DESCRIPTION OF THE DRAWINGS

The invention will now be further described with reference to the drawings, wherein.

DESCRIPTION OF PREFERRED EMBODIMENTS

Figure 1:
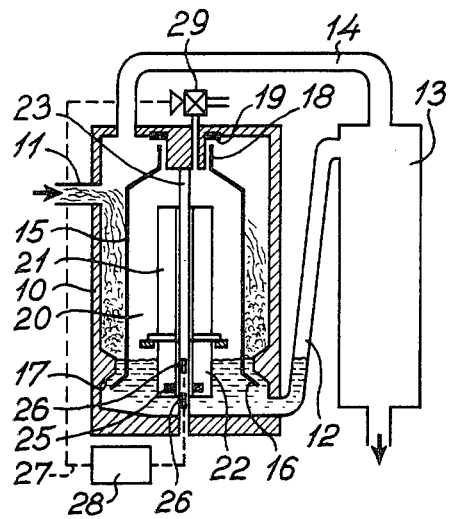
FIGS. 1 to 3 are diagrammatic sectional views of an embodiment of the apparatus according to the invention, the parts of the apparatus being shown in different stages of operation.

The metering or measuring apparatuses shown in the drawings are adapted to meter or measure the mass or weight of the milk flow passing through the conduits or lines of a milking system. Thus, the apparatuses shown may, for example, be inserted between a set of teat cups and the milk transport line of the milking system, in which line vacuum is provided in a manner known per se.

Figure 2:
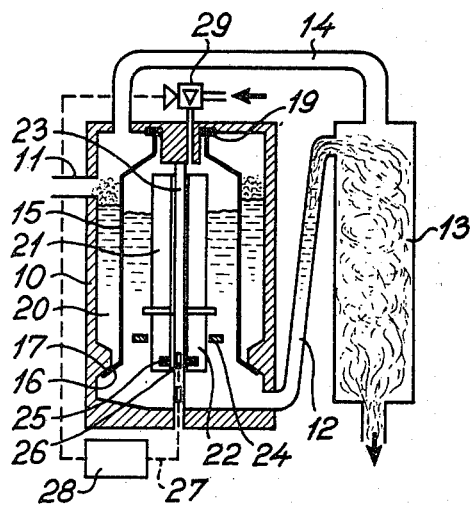
Figure 3:
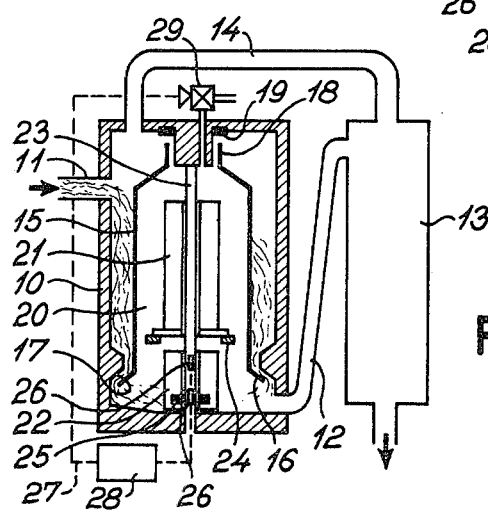

The apparatus shown in FIGS. 1 to 3 includes a housing 10 having a liquid inlet line or passage 11 connected to the upper part thereof. When the apparatus is used for measuring the yield of a milk cow the said liquid inlet line may be in communication with the teat cups used for milking the cow. The lower part of the housing 10 is connected to a liquid outlet line or passage 12 extending upwardly to a container 13 or a container-like enlargement of a vacuum line 14 communitcating with a milk transporting line (not shown) of the milking system, and also with the upper part of the housing 10. A tubular or bell-shaped valve body 15 arranged vertically movable in the housing 10 has a resilient lower rim portion 16 adapted to cooperate with and tightly engage with a downwardly facing annular valve seat 17 in the housing 10. The valve body 15 also has an upper rim portion 18 adapted to cooperate with and to sealingly engage with an annular, resilient valve seat 19. The bell-shaped valve body 15 and the part of the housing 10 positioned below the valve seat 17 define a metering or measuring chamber 20 in which a rather elongated upper float member 21 and a shorter, lower flow member 22 are mounted. The float members 21 and 22 have annular cross sections surrounding a guide rod 23 extending centrally and substantially vertically in the measuring chamber 20, and the float members may within certain limits move freely vertically along said guide rod. The lower position of the upper float member 21 is determined by a support member 24 fixed in relation to the housing 10, and a flange formed at the lower end of the float member 21 may engage with the support member as shown in FIGS. 1 and 3. The lower float member 22, which contains a magnet member 25, is in its lower position supported by the bottom of the housing 10, i.e. when no liquid is present in the metering or measuring chamber 20. The guide rod 23, which is of a non-magnetizable material, contains two vertically spaced switches or relays 26, for example so-called reed switches. These switches may via electrical conductors 27 and amplifying means 28 control a valve 29 by means of which the measuring chamber 20 may be communicated with the atmosphere.

The metering or measuring apparatus described above functions as follows:

In the starting position of the apparatus shown in FIG. 3 the bell-shaped valve body 15 is in its lower position and liquid or milk may flow from the liquid inlet passage 11 into the housing 10, past the annular valve seat 17, and into the metering chamber 20. The float members 21 and 22 are in there lower positions in which they are vertically spaced. The valve 29 is closed, and because the metering chamber 20 as well as the other part of the inner space of the housing 10 is communicating with the vacuum line 14 the total inner space of the housing 10 is under vacuum. When the liquid level in the metering or measuring chamber 20 rises the lower float member 22 eventually becomes floating in the liquid and will then be moved upwardly till it hits the lower end of the upper float member 21 as shown in FIG. 1 and the two float members 21 and 22 will now function as one coherent float member. This coherent float member will not start moving upwardly until the liquid level in the measuring chamber 20 has risen substantially more, namely up till such a level that the liquid volume displaced by the float members 21 and 22 has the same weight as that of these two float members. When the upper float member 21 has been moved a smaller distance upwardly from the support member 24 as shown in FIG. 2 the magnet member 25 in the lower float member will be positioned at the same level as the uppermost of the switches 26 which is thereby activated so as to cause transmittance of a signal to the amplifying means 28 which in turn causes opening of the valve 24 so that the measuring chamber 20 is communicated with the atmosphere. The sudden pressure rise within the metering or measuring chamber 20 causes that the bell-shaped valve body 15 is moved upwardly so that the rim portions 16 and 18 thereof are tightly engaged with their respective valve seats 17 and 19. When the supply of liquid to the measuring chamber 20 has been stopped as shown in FIG. 2 the increased pressure in the metering chamber 20 will quickly press the liquid from the metering chamber 20 out through the outlet line 12 and into the container 13 from which the liquid or milk is discharged through the milk transporting conduit or line of the milking system. When during the discharge operation the liquid level within the measuring chamber 20 eventually sinks, the floating members 21 and 22 return to their starting positions. At first the upper float member 21 will again come into engagement with and become supported by the support member 24, and when substantially all of the liquid has been pressed out of the metering chamber also the lower float member 22 will reach its lower position in which it is supported by the bottom of the housing 10. In this position the magnet member 25 surrounds the lower one of the switches 26 which is thereby activated so as to cause the valve 29 to be closed. Thereafter, the valve body 15 returns to its lower position whereby part of the liquid collected within the housing 10 outside the metering chamber 20 will flow into the metering chamber. When an amount of liquid corresponding to that just discharged has again been collected within the measuring chamber 20 the discharge operation is repeated.

It is understood, that the supply of liquid or milk through the liquid inlet line 11 to the apparatus described is divided into a number of portions having substantially the same weight despite the possible variations in the specific gravity of the liquid, for example due to a varying content of air bubbles therein. The electrical circuit controlling the valve 20 may comprise means for counting the number of discharge operations and the total amount of liquid discharged may at any time be calculated by multiplying the number of discharge operations by the mass or weight of the portion being discharged from the measuring chamber each time. This total weight or mass may, of course, be calculated by the electric circuit and directly indicated by a suitable readout or indicating device.

Figure 4:
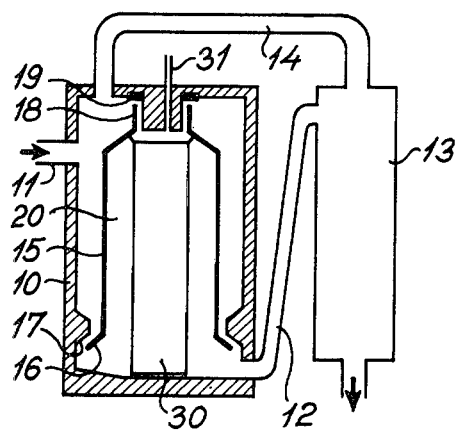
FIG. 4 is a diagrammatic sectional view of a second embodiment of the apparatus according to the invention.

FIG. 4 shows a simplified embodiment in which the two float members have been replaced by a single float member 30 on which the valve body 15 is mounted. The valve 29 and its electrical control circuit has been dispensed with and replaced by an air supply line 31 having a relatively small cross sectional area and establishing a constant communication between the metering chamber 20 and the atmosphere. When milk or another liquid flows into the housing 10 through the liquid inlet line 11 the liquid level within the metering chamber 20 and the inner of the housing 10 will rise. When the liquid level has reached a certain level at which the float member 30 and the valve body 15 mounted thereon together displace an amount of liquid having a weight corresponding to the total weight of the float member 30 and the valve body 15, the valve body 15 starts moving upwardly together with the float member 30. When the rim portions 16 and 18 of the valve body 15 approach their respective seats 17 and 19 the pressure within the metering chamber 20, which is in communication with the atmosphere through the line 31, will increase to such an extent compared with the vacuum in the remaining part of the housing 10 that the valve body 15 is suddenly pressed tightly against the valve seats 17 and 19, whereafter the amount of liquid collected within the metering chamber 20 is pressed out through the outlet line 12 as previously described. After discharge of the liquid the float member 30 and the valve body 15 mounted thereon will move back to their starting positions, whereafter another portion of liquid may flow into the metering or measuring chamber 20.

Figure 5:
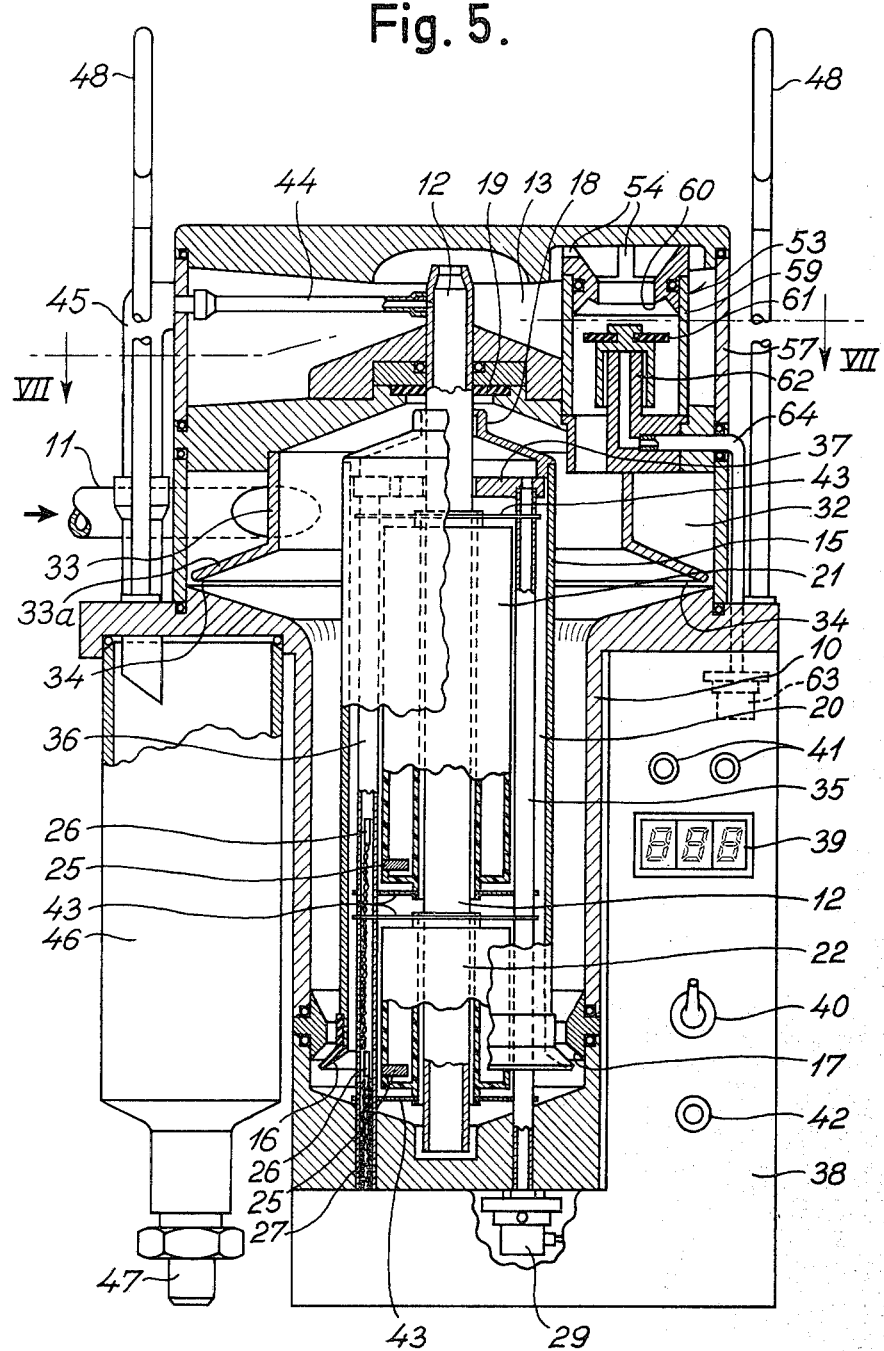
FIG. 5 is a side view and partially sectional view along the line V—V in FIG. 7 of a third embodiment of the apparatus according to the invention shown in an enlarged scale.

The embodiment shown in FIG. 5 functions in accordance with the same principle as the embodiments shown in FIGS. 1 to 4, and in order to facilitate the understanding of the apparatus shown in FIG. 5 the parts thereof corresponding to parts of the embodiments shown in FIGS. 1 to 4 have been designated with corresponding reference numerals.

In the embodiment shown in FIG. 5 the liquid inlet line or passage 11 is connected to an annular liquid inlet space 32 in the upper part of the housing 10 in such a manner that the liquid flow is supplied tangentially into the inlet space and caused to rotate therein. Radially inwardly the said annular space 32 is defined by an annular baffle plate 33 having an outwardly directed, inclined flange 33a which together with an adjacent part of the housing wall defines a relatively narrow annular space 34 functioning as a filtering slot. In FIG. 5 the discharge container 13 has the form of a discharge space formed in the upper part of the housing 10, and the liquid outlet line 12 connecting the lower part of the metering chamber 20 with said discharge space extends centrally upwardly through the metering chamber and through the float members 21 and 22 arranged therein. Thus, the discharge tube 12 is arranged similar to the guide rod 23 in the embodiments described above. The valve 29 for communicating the metering chamber 20 with the atmosphere is mounted below the metering chamber and connected to an air inlet tube 35 extending vertically upwardly through the metering chamber. A supporting plate 37 for supporting the valve body 15 in its lower position as shown in FIG. 5 is fastened to the upper ends of the air inlet tube 35 and a similar tube 36 arranged diametrically opposite to the tube 35.

The switches 26 are mounted within the tube 36 and by means of electrical conductors 27 connected to an electrical circuit which is arranged within an electronic unit 38 of the apparatus and which serves i.a. to control the valve 29. The electronic unit comprises a digital indicating device 39 which may directly indicate the weight of the amount of liquid having passed the apparatus. The electronic unit also comprises an on-off switch 40 and control lamps 41 for indicating the working conditions of the apparatus, as well as a discharge initiating contact 42 the function of which will be described in the following.

The float members 21 and 22 are not guided by a central guide rod as in the embodiments previously described, but are movably suspended by means of suspension members 43 mounted on the tubes 35 and 36 and allowing the float members to move vertically, but not horizontally as will be described more in detail in connection with FIGS. 8 and 9. A bore extending through the wall of the liquid outlet tube 12 at the upper end thereof is connected to a sample container 46 via a sampling tube 44 and a sample discharge tube 45, and the sample container 46 is provided with a manually operatable discharge valve 47 at the bottom thereof. The total apparatus may be suspended at a suitable location, for example on the milk transporting conduit of a milking system, by means of suspension hooks 48. In order to ensure uniform pressure conditions within the discharge space 13 and within the part of the inner space of the housing 10 outside the valve body 15 these spaces are interconnected via a valve device 53 opening into the discharge space 13 via openings 54 defined in a recess formed in the upper end wall of the housing 10.

Due to the tangential arrangement of the inlet tube or line 11 the milk or liquid flowing therethrough into the inlet space 32 is caused to rotate and to flow down through the filtering slot 34 as an annular liquid curtain. The amount of liquid rotating within the space 32 is influenced by an obliquely downwardly and outwardly directed force resulting from gravity and the centrifugal forces. The said obliquely directed force causes that the part of the liquid having the greatest specific weight—i.e. the liquid containing the smallest relative amount of air—is concentrated at the slot 34. Thus, the passage of the liquid through the slot 34 tends to suppress a possible foaming tendency and the slot 34 also serves to retain possible greater impurities, such as hair and the like. When the liquid level in the housing 10 and consequently also in the metering chamber 20 rises, the lower float member 22 is moved upwardly till its movement is stopped because of its engagement with the bottom surface of the upper float member 21. The two float members will not be moved upwardly together until the liquid level in the metering chamber 20 has risen to such an extent that the total buoyancy influencing the floating members 21 and 22 is sufficient partly to neutralize the total weight of the float members and partly to overcome the rather small resistance of the suspension member 43 to the vertical movement of the float members. The float members are moved upwardly a small distance till the magnet member 25 in the upper float member 21 registers with the upper switch 26. This switch will then be activated and provide a signal causing that the valve 29 is opened, whereby the metering chamber 20 is communicated with the atmosphere via the air inlet tube 35. The relative overpressure thereby created within the measuring chamber 20 will quickly move the bell-shaped valve body 15 upwardly so that its lower and upper rim portions 16 and 18, respectively, are brought into tight engagement with their respective valve seats 17 and 19. The metering chamber 20 is now tightly closed in relation to the remaining part of the inner space of the housing 10, and the atmospheric pressure within the measuring chamber will therefore quickly discharge the amount of liquid in the measuring chamber upwardly through the central liquid outlet tube 12 into the discharge space 13. A smaller, but representative part of the amount of liquid discharged through the tube 12 will be pressed into the sampling tube 44 from which it flows through the discharge tube 45 down into the sample container 46. From a depression 55 in the bottom of the discharge space 13 milk or liquid is sucked upwardly through the vacuum line 14 and into the milk transporting conduit of the milking system in connection with which the metering apparatus may be used. The end of the vacuum line 14 extending into the space 13 is surrounded by a partcylindrical guard plate 56, FIGS. 6 and 7, the side edges of which are arranged in such a distance from the peripheral wall 57 of the space 13 that narrow slots 58 are defined between said side edges of the guard plate 56 and the said peripheral wall 57. When a portion of liquid is discharged from the metering chamber 20 through the liquid outlet tube 12 the liquid flows through the slots 58 into the depression 55 at a rate of flow which is smaller than the aspiration capacity of the vacuum line 14. As a consequence, a substantial amount of air is sucked into the vacuum line 14 together with the liquid and mixed therewith. If the liquid had been sucked up through the vacuum line as coherent liquid columns, this would cause disadvantageous transitory reductions of the vacuum at the teat cups when the apparatus is used in connection with a milking machine or milking system.

When the liquid level in the metering or measuring chamber 20 is sinking due to the above described discharge through the vacuum line 14 that float members 21 and 22 are jointly moved downwardly till the upper float member 21 reaches its lower position, and thereafter the lower float member 22 continues its downward movement to its lower position. When the magnet member 25 arranged in the float member 22 passes the lower switch 26 this switch will be activated and provide a signal causing the valve 29 to close and disconnect the connection between the metering chamber 20 and the atmosphere. Thereafter, the valve body 15 falls back to its lower position so that the metering chamber 20 may be filled with a further portion of milk or another liquid.

Figure 6:
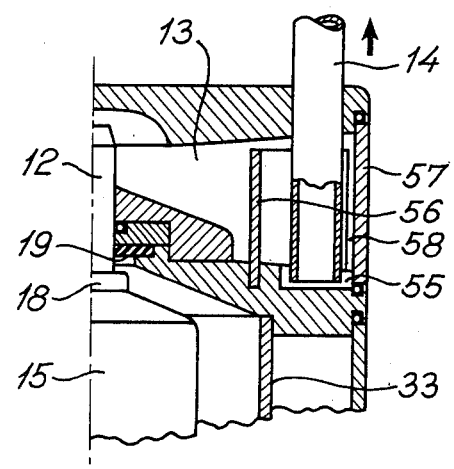
FIG. 6 is a sectional view along the line VI—VI in FIG. 7 in the apparatus shown in FIG. 5.
Figure 7:
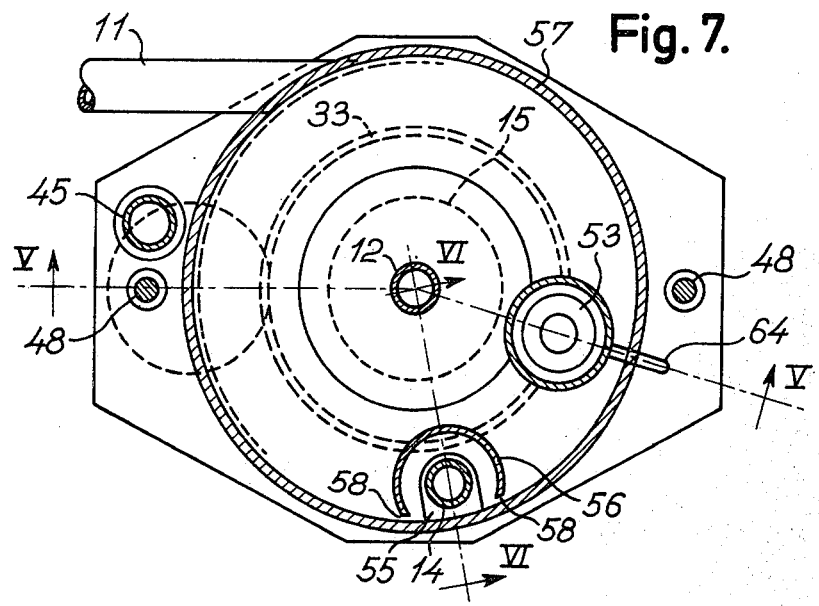
FIG. 7 is a cross sectional view along the line VII—VII in FIG. 5.

Also in the embodiments shown in FIGS. 5 to 7 the mass or weight of the liquid flowing through the apparatus is in fact measured by counting the number of portions discharged from the metering chamber 20. When the flow of liquid to be metered stops, for example because the milking of a cow is finished, the metering chamber 20 will normally contain a certain amount of liquid which is insufficient to start the normal discharge operation described above. If this residual amount is not discharged from the measuring chamber it will descrease the accuracy of measurement of the first as well as the subsequent metering of a liquid flow. Furthermore, mixing of the residual amount from a previous measurement with the amount of liquid being metered in a subsequent measuring operation may be undesired for several reasons. In the embodiment shown in FIG. 5 the residual amount may be discharged by means of the valve device 53. This valve device has a valve housing 59 having a valve seat 60 at its upper end, and a movable valve member 61 having a downwardly extending cylindrical skirt surrounding a vertical air inlet stub 62 connected to a magnetic valve 63 by means of a connecting conduit 64. When it is desired to discharge a residual amount of liquid collected in the metering or measuring chamber 20 the discharge initiating contact 42 is activated manually which causes that the magnetic valve 63 is opened so that the connecting conduit 64 and the air inlet stub 62 are communicated with the atmosphere. Air will then flow through the air inlet stub 62 whereby the valve member 61 is blown upwardly against its seat 60. As the space above the valve seat is exposed to vacuum while the bottom surface of the valve member 61 is exposed to a pressure which is substantially equal to atmospheric pressure the valve member 61 will remain sucked against its valve seat 60. The atmospheric pressure spreads from the inlet stub 62 to the metering chamber 20 and to the inner space of the housing 10 except for the discharge space 13 which is exposed to vacuum. The difference in pressure causes that the total residual amount of liquid is pressed from the metering chamber 20 and the surrounding chamber of the housing upwardly through the outlet tube 12 and into the discharge space 13. When the liquid has been totally discharged from the metering chamber 20 the lower float member 21 has sunk to the level at which the lower switch 26 is activated, which causes that the magnetic valve 63 is closed. The pressure conditions will then once again become uniform all over in the inner space of the apparatus, and the valve member 61 will therefore fall back to its starting position in which it is supported by the air inlet stub 62 as shown in FIG. 5. The weight or mass of the residual amount of liquid discharged may be determined on the basis of the period of time lapsing from the moment at which the contact 42 is activated manually till the moment at which the magnet member 25 of the lower float member 22 activates the lower switch 26, empirically determined reaction times of the valve device 53 and other parts of the apparatus being taken into consideration. Calculation of the weight or mass of the residual amount on the basis of said discharge time is conveniently made by the electronic unit 38 of the apparatus, which may also conveniently automatically add the weight of the said residual amount to the weight of the liquid determined by counting the number of discharged liquid portions.

Figure 8:
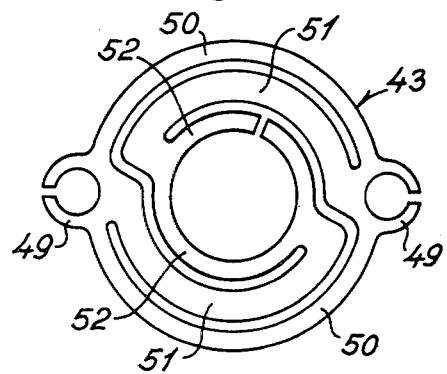
FIG. 8 is a plan view of a suspension member for movable suspension of the floating members of the apparatus.

FIG. 8 shows a first embodiment of the suspension members 42 used for movable suspension of the float members 21 and 22 along the tubes 35 and 36 in the apparatus shown in FIG. 5. The suspension member 43, which may, for example, be punched out from a thin resilient plate of steel or other metal, has a substantially circular shape provided with two slitted mounting ears 49 surrounding each one of the tubes 35 and 36 in the mounted condition of the suspension member. The punching pattern is chosen so that the suspension member 43 consists of an annular outer frame portion 50 which is provided with the ears 49, and two oppositely directed, circularly curved suspension arms 51 extending from said ears 49 and having "free" ends interconnected by means of an inner slitted mounting ring 52 adapted to be mounted on the end portions of the float members. It is understood, that the arms 51 will offer a great resistance to deflection in the plane of the suspension member 43, while they will offer no substantial resistance to deflection in a direction perpendicular to said plane.

Figure 9:
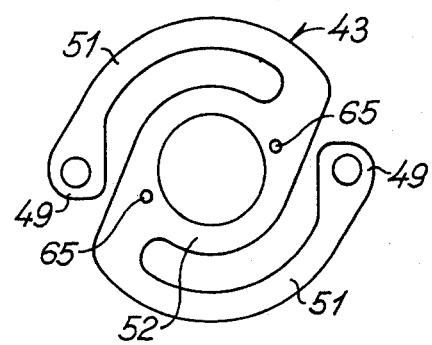
FIG. 9 is a further embodiment of the suspension member.

FIG. 9 shows another embodiment of the suspension members 43. The annular outer frame portion 50 has been dispensed with and the ears 49 as well as the mounting ring 52 are not slitted. In return the mounting ring 52 is provided with a pair of diametrically oppositely arranged small circular openings 65 for receiving screws or other fastening means for fastening the mounting ring to a float member.

Figure 10:
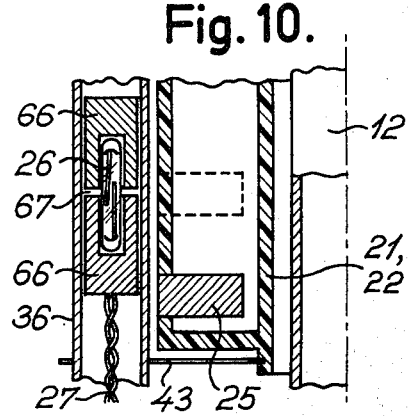
FIG. 10 is a fragmentary sectional view of the apparatus shown in FIG. 5, illustrating a reed switch and a switch actuating magnet cooperating therewith.

It has been found that a substantially increased accuracy in the level detection made by the reed switches 26 and the magnet member 25 cooperating therewith may be obtained if each switch is surrounded by a magnetizable material, such as an iron block 66, which is separated by a substantially horizontal, narrow slot 67, vide FIG. 10. The magnetizable block 66 and the contacts of the switch 26, which is also of a magnetizable material, then causes that the magnetic field generated by the magnet member 25 obtains such a form around the switch 26 that the switch will be actuated and closed only when the magnet member 25 takes up the position which is shown in dotted lines and in which the magnet member is exactly registering with the slot 67.

FIGS. 11 to 14 illustrate the presently most preferred embodiment of the apparatus according to the invention. As the function of this preferred embodiment corresponds to the function of the embodiment shown in FIGS. 5 to 10 in many respects, corresponding parts have been designated by corresponding reference numerals. In the embodiment shown in FIGS. 11 to 14 the annular baffle plate 33 has a cylindrical skirt 68 extending downwardly from the flange 33a and having a serrated lower edge portion 69 engaging with the outer wall of the housing 10. An annular pattern of foam openings 70 in the cylindrical skirt 68 is positioned immediately below the flange 33a, and an air slot 71 is defined between the edge of the baffle plate 33 and an adjacent end wall 72 of the housing. The valve 29 is a three-way valve connected to conduits 73 and 74 communicating with the atmosphere and a vacuum source, such as the vacuum line of a milking system, respectively. The air inlet tube 35 connects valve 29 with an annular space 75 defined between the top surface of the supporting member 37 and an expansible annular channel member 76 engaging with the top wall of the valve body 15, vide FIG. 12. The top wall of the valve body 15 contains a connecting bore 77 and the top wall 72 of the housing 10 is penetrated by a vertically extending connecting tube 78 having a protecting cap 79 at its upper free end within the discharge space 13. The supporting member 37 contains a one-way or non-return valve 80 having a valve member 81 and a spring member 82 tending to move the valve member 81 to its closed position, vide FIG. 12. The tube 36 which is made from a non-magnetizable material, such as stainless steel, contains three switches 26, for examples reed switches. The two uppermost switches 26 are closely vertically spaced and may, for example, have a vertical spacing of about 7 mm for a purpose which will be described below.

Figure 11:
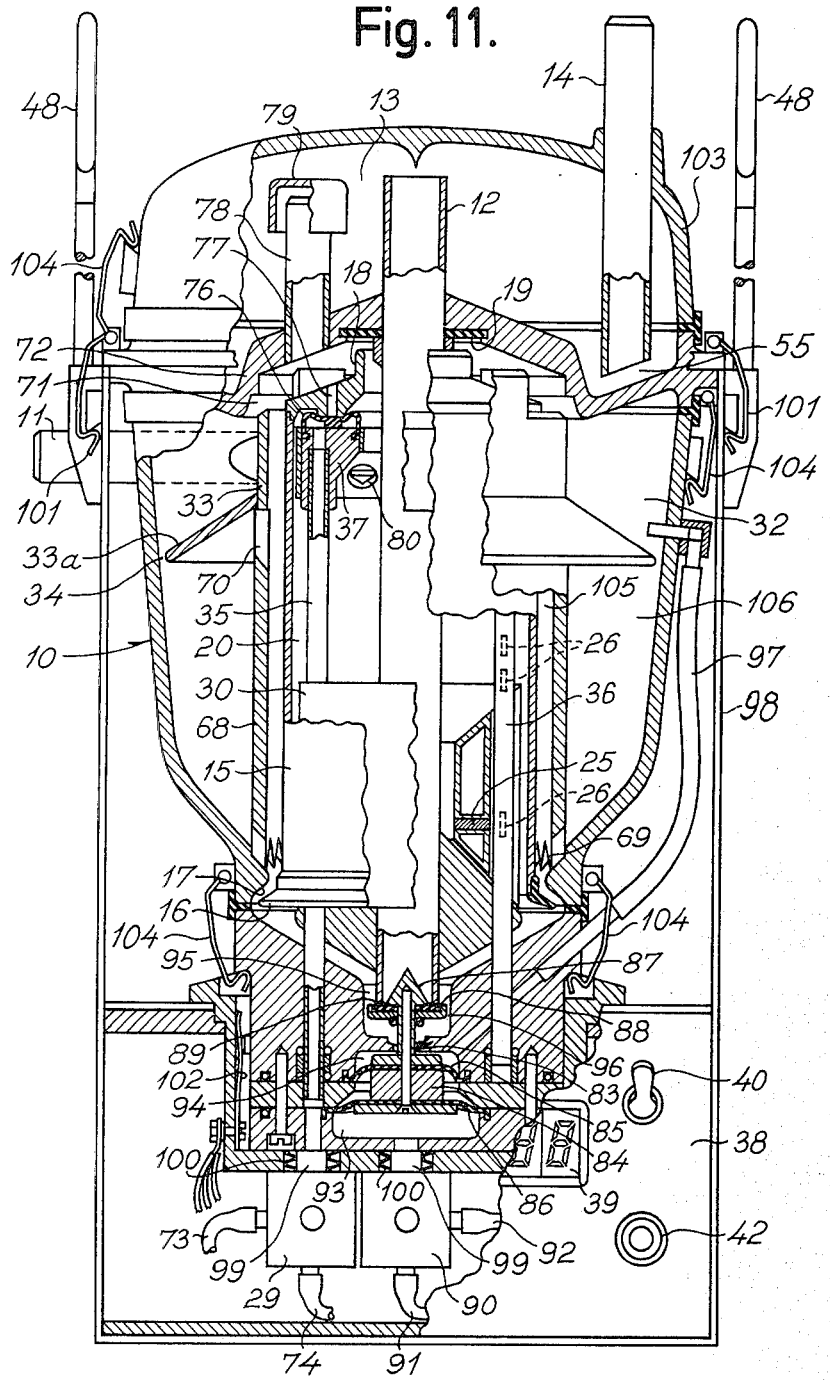
FIG. 11 is a side view and partially sectional view of a fourth embodiment of the apparatus according to the invention.

In the embodiment shown in FIGS. 11 to 14 the valve device 53 in FIG. 5 is replaced by a valve device 83 by means of which the lower end of the liquid outlet tube 12 may be opened and closed. The valve device 83 comprises a valve member 84 mounted so as to be movable in a vertical direction by means of resilient diaphragms 85 and 86. The valve member 84 includes a guide cone 87 and a resilient disc 88 cooperating with the lower edge 89 of the outlet tube 12 serving as annular valve seat. Movement of the valve member 84 is controlled by a three-way valve 90 which may be of the same type as the valve 29 and which communicate with the atmosphere and with a vacuum source, such as the vacuum line of a milking system, respectively. Thus, valve 90 may selectively supply vacuum or atmospheric pressure to a valve chamber 93 in which the top wall is constituted by the lower diaphragm 86. The upper diaphragm 85 constitutes the bottom wall of a liquid chamber 94, and the lower end of the outlet tube 12 extends downwardly into a recess 95 formed in the bottom part of the housing 10. The liquid chamber 94 is in communication with the recess 95 through a bypass passage 96 when the valve member 84 is in its upper position in which it closes the lower end of the outlet tube 12 as shown in FIG. 11, while the bypass switch 96 is closed when the valve member 84 is in its lower position. The liquid chamber 94 is in communication with the liquid inlet space 32 through a return conduit 97.

The housing 10 is arranged in an outer holder 98 provided with the suspension hooks 48 and containing the electronic unit 38 and the valves 29 and 90. Each of these valves has a tube stub 99 which is sealingly received in an annular sealing bellows 100 or another suitable sealing device when the housing 10 is inserted in the outer holder 98 to which it may be detachably fastened by means of releasable fastening devices 101. When the housing 10 is arranged in the holder 98 electrical connection between the switches 26 and the electronic unit 38 is established by means of electrical contact members 102.

A lid or cover 103 forming the top wall of the discharge space 13, as well as other parts of the housing 10 may be interconnected by means of releasable latching members 104, whereby the inner space of the housing is easily accessible for cleaning etc.

The function of the apparatus shown in FIG. 11 will now be described. In the starting position of the apparatus the three-way valve 90 connects the valve chamber 93 to the atmosphere through the conduit 91 so that the valve chamber 93 is exposed to atmospheric pressure pushing the resilient lower diaphragm 86 upwardly so that the resilient disc 88 of the valve member 84 is pressed into tight engagement with the lower edge 89 of the discharge tube 12 as shown in FIG. 11. The valve 29 communicates the air inlet tube 35 with the vacuum conduit 74 so that the annular space 75 defined by the resilient channel member 76 is exposed to vacuum whereby the channel member is in its collapsed condition shown in FIG. 11. As the valve body 15 is supported by the channel member 76 the valve body 15 is in its open position as shown in FIG. 11. The inner space of the housing 10 outside the valve body 15 is divided by the shirt 68 into inner and outer annular chambers 105 and 106, respectively. The inner chamber 105 is in constant communication with the discharge space 13 and the vacuum line 14 through the connecting tube 78, and the inner and outer chambers 105 and 106 are interconnected as well through the air slot 71 as through the foam openings 70. Furthermore, in the open position of the valve body 15 the metering or measuring chamber 20 is in communication with the inner chamber 105 through a lower valve slot defined between the rim portion 16 and the valve seat 17, and through another valve slot defined between the rim portion 18 and the valve seat 19. Consequently, all of the chambers 20, 105, and 106 are exposed to vacuum when the valve body 15 is in its open position as shown in FIG. 11.

Figure 12:
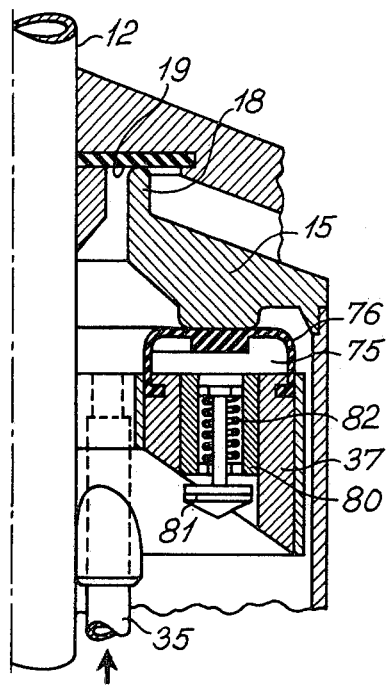
FIG. 12 is a fragmentary sectional view of the apparatus illustrated in FIG. 11 showing a one-way valve.

A flow of liquid or milk being passed tangentially into the liquid inlet space 32 through the liquid inlet tube or line 11 flows downwardly through the filtering slot 34 as a liquid curtain as described above in connection with the embodiment of FIG. 5. The inflowing liquid continues downwardly past the serrated edge portion 69 of the skirt 68 and past the annular valve seat 17 into the metering chamber 20. As the liquid level in the metering chamber rises the float member 30 will be moved upwardly. When the float member reaches an upper position in which the magnet member 25 is positioned at the same level as the uppermost of the reed switches 26 this switch is actuated so as to provide an output signal causing the three-way valve 29 to disconnect the communication with the vacuum conduit 74 and to establish communication with the atmosphere through the conduit 73. Thus, atmospheric pressure is supplied to the annular space 75 through the tube 35 whereby the channel member 76 is expanded as shown in FIG. 12, and the valve body 15 supported by the channel member 76 is lifted to its closed position in which as well the upper valve 18, 19 as the lower valve 16, 17 are closed. The one-way or non-return valve 80 is then exposed to atmospheric pressure and opened so that also the metering or measuring chamber 20 is exposed to atmospheric pressure. The outlet tube 12 is closed by the valve device 83 while the bypass passage 96 connects the metering chamber 20 with the liquid chamber 94 which is under vacuum. Consequently, liquid or milk will be pressed out of the metering chamber through the bypass passage having a small cross sectional area, and liquid will be sucked from the chamber 94 and returned to the inlet space through the return conduit 97. This initial slow discharge operation wherein the liquid or milk is exposed to atmospheric pressure contributes to suppression of foam. During this initial discharge the liquid level within the metering chamber 20, and the float member 30 will sink slowly. When the magnet member 25 has reached the same level as that of the next reed switch 26, this switch is actuated so as to generate an output signal causing valve 90 to disconnect communication between the valve chamber 93 and the atmosphere and to establish communication with the vacuum conduit 92. Thereby the valve member 84 is moved to its open position and the remaining amount of liquid within the metering chamber 20 is dicharged through the outlet conduit 12. When the float member 30 has reached the position shown in FIG. 11 in which the magnet member 25 is at the same level as the lower reed switch 26, this reed switch will be actuated so as to generate an output signal causing the valve 29 to supply vacuum to the annular space 75, whereby the channel member 76 is moved to its collapsed position shown in FIG. 11. As the valve body 15 is supported by the channel member 76, the valve body is moved to its lower, open position and the bore 77 secures that the gas pressure within the space defined between the channel member 76 and the top wall of the valve body 15 is the same as that of the annular chamber 105. The output signal from the lower switch 26 also causes the valve 90 to expose the valve chamber 93 to atmospheric pressure so that the outlet tube 12 is closed by valve device 82. The apparatus is now in its starting position, and the operation just described may be repeated.

It is understood, that the apparatus described will function so as to discharge liquid from the metering chamber 20 in exactly metered portions having substantially the same mass or weight. Consequently, the total mass of the liquid passed through the apparatus may be calculated by counting the number of portions and by multiplying this number with the weight or mass of each portion. However, when the flow of liquid supplied to the apparatus stops the apparatus may contain a residual amount of liquid which is not sufficient to obtain the liquid level within the metering chamber 20 starting the discharge operation. Discharge of such residual amount of liquid from the metering chamber may be started by manually operating the contact 42. Such operation of the contact 42 causes the valve 29 to supply atmospheric pressure to the annular space 75 while the valve device 83 remains in its closed position. Thus, the residual amount of liquid contained in the measuring chamber 20 will be discharged through the bypass passage 96, and the amount of the liquid discharged from the metering chamber as well as that remaining in chambers 105 and 106 may be determined by the electronic unit 38 on the basis of the time lapsing from the moment at which the contact 42 is actuated to the moment at which the lower reed switch 26 is actuated by the magnet member 25. In order to remove the residual liquid from the chambers 105 and 106 the apparatus may thereafter automatically perform a number, for example six, consecutive discharge operations. The total amount of the liquid flow having passed the apparatus may be indicated by the digital indicating device 39, and the apparatus is now ready for another measurement.

Figure 14:
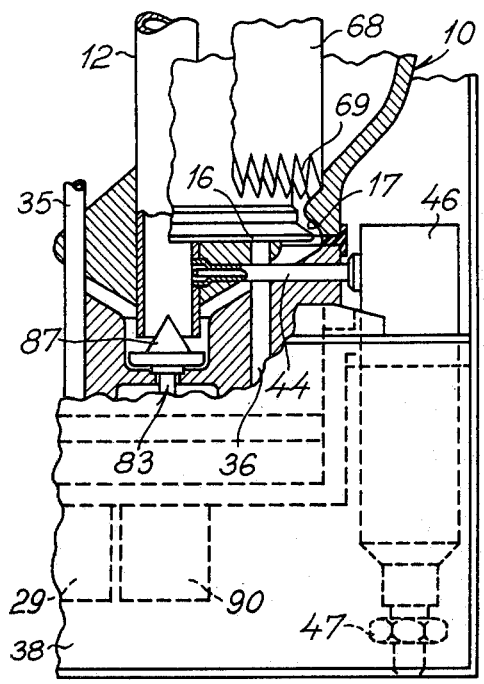
FIG. 14 is a fragmentary side view, partly in section, illustrating a modification of the apparatus shown in FIG. 11.

The apparatus of FIG. 11 may be provided with a sampling device as shown in FIG. 14 and functioning in substantially the same manner as the sampling device described in connection with the embodiment shown in FIG. 5.

Figure 13:
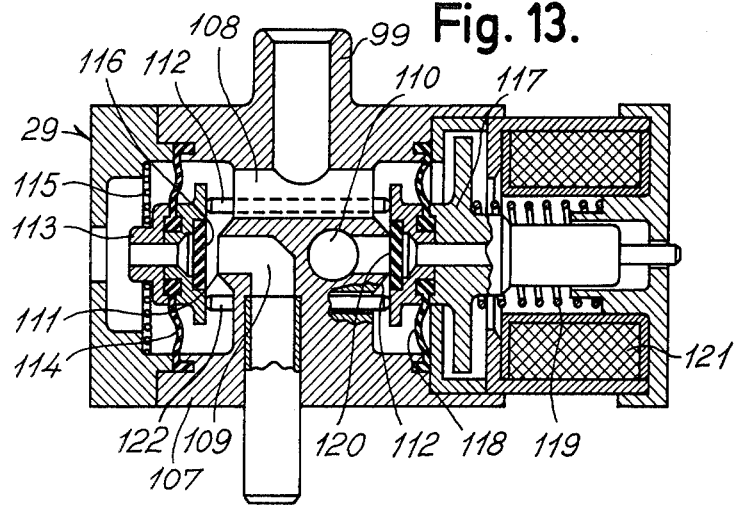
FIG. 13 is a sectional view in an enlarged scale of a gas valve device.

The valves 29 and 30 may be of the type shown in FIG. 13. The valve mechanism shown comprises a housing 107 defining an inner valve chamber 108 which is in communication with the passage defined by the tube stub 99. The housing also defines a vacuum passage 109 which is connected to the vacuum line 74, and a passage 110 which is in communication with the atmosphere through the conduit 73 shown in FIG. 11. The passages 109 and 110 open into the valve chamber 108 in opposite directions and are surrounded by valve seats 111 and 112, respectively. A valve member 113 is suspended in a diaphragm 114 and a spring member 115 so as to be movable between an open position shown in FIG. 13 and a closed position in which a resilient sealing disc 116 tightly engages with the valve seat 111 and closes the vacuum passage 109. Similarly, the valve seat 112 is controlled by a valve member 117 suspended by a diaphragm 118 and biased towards its closed position by a coil spring 119, in which a sealing disc 120 tightly engages with the valve seat 112 and closes the passage 110. The valve member 117 may be moved to an open position (to the right in FIG. 13) by energizing a magnetic coil 121, and the valve member 113 is simultaneously moved to its closed position under the bias of the spring member 115. When the magnetic coil 121 is deenergized the valve member 117 will return to its closed position under the bias of the coil spring 119, and the valve member will simultaneously be moved to its open position against the bias of the spring member 115 because axially movable distance pins 122 secure a constant axial spacing of the valve members 113 and 117.

It should be understood, that various modifications and changes of the embodiments described above may be made within the scope of the present invention. As an example, different types of valve devices may be used for controlling the discharge of liquid from the metering chamber 20 in portions having substantially the same weight. It should also be understood that while the invention has especially been described in connection with metering a flow of milk in a milking system the invention could also be used for measuring a flow of any other type of liquid. Furthermore, liquid may be discharged from the metering chamber by means of pressurized gas so that the apparatus need not necessarily be driven by vacuum supplied from a vacuum source.

We claim:

1. A method of metering a liquid flow, said method comprising:
(a) passing said liquid flow into a metering or measuring chamber containing floating means movably arranged therein andincluding liquid inlet and outlet passages, said outlet passage opening into said measuring chamber at the lower part thereof,
(b) discharging said liquid from said measuring chamber through said outlet passage in portions, the discharge of each portion being initiated in response to movement of said floating means to a predetermined upper level and caused by closing said liquid inlet passage and exposing said measuring chamber to a gas pressure exceeding the pressure at the discharge end of said outlet passage, and
(c) counting the number of portions discharged, the supply of gas pressure to said measuring chamber being initiated when said floating means has been moved upwardly to a predetermined first level, whereafter liquid is initially discharged from said chamber through a small bypass opening communicating with said liquid inlet passage, communication being established between said measuring chamber and a discharge end of the outlet passage when said floating means has reached a predetermined lower second level, whereby the liquid portion remaining in the measuring chamber is discharged through said outlet passage.

2. A method according to claim 1, wherein the function of inlet valve means arranged in said liquid inlet passage is controlled by the position of said floating means in said measuring chamber.

3. A method according claim 2, wherein said measuring chamber is exposed to atmospheric pressure, while the discharge end of said outlet passage is exposed to vacuum.

4. A method according to claim 2, wherein said inlet valve means comprise an inlet valve member movable between opening and closing positions, said inlet valve member being moved to its closing position by means of said gas pressure supplied to said measuring chamber.

5. A method according to claim 3, wherein a sample of each liquid portion discharged from said measuring chamber is taken through a sample conduit branched off from said outlet passage.

6. A method according to claim 1, wherein the function of outlet valve means arranged in said liquid outlet passage and including an outlet valve member movable between an opening and a closing position is also controlled by the position of said floating means in said measuring chamber, said communication being established by moving said outlet valve member to its opening position.

7. A method according to claim 1, wherein the amount of a possible last fraction of a liquid portion passed into said measuring chamber is determined on the basis of the time used for discharging said last fraction from the measuring chamber.

8. A method according to claim 7, wherein the discharge of said last fraction is initiated manually.

9. A method according to claim 1, wherein the amount of a possible last fraction of a liquid portion passed into said measuring chamber is determined on the basis of the time used for discharging said last fraction through said bypass opening.

10. A method of metering milk flowing from the teat cups of a milking machine, said method comprising:
(a) passing said milk into a metering or measuring chamber containing floating means movably arranged therein, and including liquid inlet and liquid outlet passages, said outlet passage opening into said measuring chamber at the lower part thereof,
(b) discharging said milk from said measuring chamber through said outlet passages in portions, the discharge of each portion being initiated in response to movement of said floating means to a predetermined upper level and caused by closing said liquid inlet passage and exposing said measuring chamber to atmospheric pressure while the discharge end of said outlet passage is communicated with the vacuum conduit of said milking machine, and
(c) counting the number of portions discharged, the supply of atmospheric pressure to said measuring chamber being initiated when said floating means has been moved upwardly to a predetermined first level, whereafter milk is initially discharged from said chamber through a small bypass opening communicating with said liquid inlet passage, communication being established between said measuring chamber and a discharge end of said outlet passage when said floating means has reached a predetermined second lower level, whereby the liquid portion remaining in the measuring chamber is discharged through said outlet passage.

11. A method according to claim 10, wherein the function of inlet valve means arranged in said liquid inlet passage is controlled by the position of said floating means in said measuring chamber.

12. A method according to claim 11, wherein said inlet valve means comprise an inlet valve member movable between opening and closing positions, said inlet valve member being moved to its closing position by means of said atmospheric pressure to which the measuring chamber is exposed.

13. A method according to claim 10, wherein the function of outlet valve means arranged in said outlet passage and including an outlet valve member movable between an opening and a closing position, is also controlled by the position of said floating means in said measuring chamber, said communication being established by moving said outlet valve member to its opening position.

14. A method according to claim 10, wherein said milk is discharged from the measuring chamber through an outlet passage extending to a discharge end at a level above the maximum milk level in the measuring chamber.

15. A method according to claim 10, wherein air is separated from milk supplied to said measuring chamber, while air is mixed with milk discharged therefrom.

16. A method according to claim 15, wherein the amount of a possible last fraction of a milk portion passed into said measuring chamber is determined on the basis of the time used for discharging said fraction from the measuring chamber, the discharge of said last fraction being initiated manually.

17. A method according to claim 16, wherein said possible last fraction is discharged through said bypass opening.

18. A method according to claim 10, wherein a small sample fraction of each milk portion discharged from said measuring chamber is taken out through a sample conduit branched off from said outlet passage.

19. An apparatus for metering a liquid flow, said apparatus comprising:
(a) a metering or measuring chamber having liquid inlet and outlet passages, said outlet passage opening into the lower part of said measuring chamber,
(b) floating means movably arranged within said chamber,
(c) discharge means for discharging said liquid from said measuring chamber through said outlet passage in portions, said discharge means being adapted to initiate discharge of each portion in response to movement of said floating means to a predetermined upper level by closing said liquid inlet passage and exposing said measuring chamber to a gas pressure exceeding the pressure at the discharge end of said outlet passage, said discharge means comprising a valve body for controlling said inlet passage and movable to an inlet passage closing position by the gas pressure supplied to said measuring chamber, said discharge means further comprising gas valve means controlled by said floating means so as to supply said gas pressure to the measuring chamber when said floating means has reached a predetermined upper position, said inlet valve body being shaped so as to define the upper part of said measuring chamber, a lower annular portion of said valve body being adapted to cooperate with a downwardly facing annular valve seat, and
(d) means for counting the number of portions discharged.

20. An apparatus according to claim 19, further comprising electric relays or switches which may be actuated by magnetic forces and which are arranged at different levels along said measuring chamber for controlling the function of said discharge means, said floating means comprising magnetic means for actuating said switches or relays.

21. An apparatus according to claim 20, wherein each switch or relay is surrounded by a magnetizable material separated by a substantially horizontal, narrow slot.

22. An apparatus according to claim 19, further comprising guide means for allowing said floating means to move vertically and for substantially preventing horizontal movement thereof.

23. An apparatus according to claim 22, wherein said guide means comprise guide columns extending axially into said measuring chamber and supporting said valve body in its lower, inlet opening position.

24. An apparatus according to claim 23, wherein at least one of said columns is tubular, the hollow inner space thereof forming part of a gas flow path from said gas valve means to said measuring chamber.

25. An apparatus according to claim 24, wherein said gas flow path contains a valve device closing said flow path when said valve body is in its lower, inlet opening position, and opening said flow path when said valve body is in its upper, inlet closing position.

26. An apparatus according to claim 25, wherein said flow path further contains a one-way or non-return valve downstream of said valve device.

27. An apparatus according to claim 19, further comprising a small bypass passage connecting the lower part of said measuring chamber with said liquid inlet passage, said discharge means further comprising an outlet valve member for controlling said outlet passage and movable between opening and closing positions, and means for moving said outlet valve member to its opening position a short period of time after supplying gas pressure to said measuring chamber by means of said gas valve.

28. An apparatus according to claim 27, further comprising manually operatable means for initiating discharge of a possible last fraction of a liquid portion from said measuring chamber through said bypass passage, and means for determining the amount of said fraction on the basis of the time used for discharging the same.

29. An apparatus according to claim 19, wherein said outlet passage extends to a discharge end thereof at a level above the maximum liquid level in the measuring chamber.

30. An apparatus according to claim 19, further comprising manually operatable means for initiating discharge of a possible last fraction of a liquid portion from said measuring chamber, and means for determining the amount of said fraction on the basis of the time used for discharging said fraction.

31. An apparatus according to claim 19, further comprising a sampling conduit branched off from said outlet passage.

32. An apparatus according to claim 19, wherein said inlet passage is adapted to be connected to teat cups of a milking machine, while said outlet passage is adapted to be connected to a vacuum line of said milking machine.

33. An apparatus according to claim 32, further comprising means for connecting said measuring chamber to said vacuum line when said liquid inlet passage is open.

34. An apparatus according to claim 33, further comprising means arranged upstream of said measuring chamber for separating air from milk, and means downstream of said measuring chamber for mixing air into milk discharged through the outlet passage.

35. An apparatus according to claim 34, wherein said inlet passage comprises an annular space surrounding said measuring chamber, said air separating means being arranged in said annular space.

36. An apparatus for metering a liquid flow, said apparatus comprising:
(a) a measuring chamber having a liquid inlet passage, a liquid outlet passage, and an upper venting passage, said outlet and venting passages being exposed to vacuum,
(b) a tubular valve body defining the upper part of said measuring chamber therein, said valve body having a lower annular valve body portion cooperating with a downwardly facing annular inlet valve seat, and an upper annular valve body portion having a smaller diameter than said lower valve body portion and cooperating with a downwardly facing venting valve seat,
(c) floating means movably arranged within said measuring chamber,
(d) valve means for connecting said measuring chamber to the atmosphere in response to upward movement of said floating means to a predetermined upper level, whereby said tubular valve body is moved to an upper portion in which said valve body portions engage with their corresponding valve seats, and for disconnecting the measuring chamber from the atmosphere in response to downward movement of said floating means to a predetermined lower level, whereby said tubular valve body is moved to a lower position in which said valve body portions are out of engagement with their corresponding valve seats so that the measuring chamber is in communication with said inlet and venting passages.

37. An apparatus according to claim 36, further comprising guide columns for allowing said floating means to move vertically and for substantially preventing horizontal movement thereof, said guide columns supporting said valve body in its said lower position.

38. An apparatus according to claim 37, wherein at least one of said columns is tubular, the hollow inner space thereof forming part of a gas flow path from said gas valve means to said measuring chamber.

39. An apparatus according to claim 38, wherein said gas flow path contains a valve device closing said flow path when said valve body is in its lower position and opening said flow path when said valve body is in its upper position.

40. An apparatus according to claim 36, further comprising a small bypass passage connecting the lower part of said measuring chamber with said liquid inlet passage, an outlet valve member controlling said outlet passage being movable between opening and closing positions, and means for moving said outlet valve member to its opening position in response to downward movement of the floating means to a level spaced a small distance below said upper level.

41. An apparatus according to claim 40, further comprising manually operatable means for initiating discharge of liquid from the measuring chamber through said bypass passage, and means for determining the amount of liquid discharged on the basis of discharge time.

42. An apparatus according to claim 36, wherein said inlet passage comprises an annular space surrounding said measuring chamber, means for separating air from liquid being arranged in said annular space.

43. A method of metering a liquid flow, said method comprising:
(a) feeding said liquid flow into a metering or measuring chamber in which a first pressure is maintained;
(b) sensing the liquid level in said chamber;
(c) interrupting said feed of liquid into the metering or measuring chamber and exposing the liquid therein to an increased second pressure in response to the sensing of a predetermined first liquid level in said chamber,
(d) maintaining said increased pressure in said chamber during a time interval so as to reduce the volume of gas contained in the liquid in that chamber,
(e) discharging liquid from said chamber, and
(f) determining the amount of liquid being discharged from said chamber, on the basis of the liquid level sensed after lapse of said time interval but prior to initiating said discharge.

44. A method according to claim 43, wherein said first pressure is a vacuum, while said increased second pressure is atmospheric pressure.

45. A method according to claim 43, wherein the liquid level in said chamber is sensed by floating means movably arranged in that chamber.

46. A method according to claim 43, wherein liquid is returned from said chamber to the liquid feed through a small bypass opening during said time interval, said discharge being initiated in response to the sensing of a predetermined second lower liquid level in said chamber.

47. A method according to claims 43, 44, 45, or 46, wherein said interruption of feed of liquid to said chamber is caused by moving an inlet valve member controlling said feed, to a closed position under the influence of said increased second pressure when supplied to said chamber.

48. An apparatus for metering a liquid being fed into a metering or measuring chamber, said apparatus comprising:
(a) level sensing means for sensing the liquid level within said measuring chamber;
(b) means for interrupting the feed of liquid into said chamber and for increasing the pressure within said chamber during a period of time, said feed interrupting and pressure increasing means being controlled by said level sensing means,
(c) means for discharging liquid from said chamber when said time period has lapsed, and
(d) means for determining the amount of liquid being discharged from said chamber, on the basis of the liquid level sensed after lapse of said time period but prior to initiating said discharge.

* * * * *